United States Patent [19]

Vincent et al.

[11] Patent Number: 5,070,557
[45] Date of Patent: Dec. 10, 1991

[54] PROTECTIVE RESTRAINT FOR ALZHEIMER AND OTHER PATIENTS

[76] Inventors: Barbara J. Vincent, 102 Harrison; Wanda G. Hale, P.O. Box 73, both of Burlington, Iowa 52601

[21] Appl. No.: 571,788

[22] Filed: Aug. 24, 1990

[51] Int. Cl.$^5$ .............................................. A47C 27/08
[52] U.S. Cl. .......................................... 5/424; 5/494; 128/872
[58] Field of Search .................... 5/424, 494, 495, 496, 5/498; 128/869, 870, 872

[56] References Cited

U.S. PATENT DOCUMENTS

| | | | |
|---|---|---|---|
| 1,368,582 | 2/1921 | Stevens | 5/494 |
| 2,239,017 | 4/1941 | Roberts | 5/498 |
| 2,700,778 | 2/1955 | Syracuse | 5/494 |
| 2,912,977 | 11/1959 | Holbrook | 5/494 |
| 2,927,581 | 3/1960 | Queen | 5/424 |
| 3,134,110 | 5/1964 | Gamichon | 5/498 |
| 3,245,382 | 4/1966 | Easley | 5/424 |
| 3,857,124 | 12/1974 | Hadley | 5/494 |
| 4,161,044 | 7/1979 | Bogle | 5/494 |
| 4,742,821 | 5/1988 | Wootan | 5/424 |
| 4,853,996 | 8/1989 | Harrigan | 5/494 |

FOREIGN PATENT DOCUMENTS

| | | | |
|---|---|---|---|
| 335536 | 10/1989 | European Pat. Off. | 128/870 |
| 2261748 | 9/1975 | France | 5/424 |

*Primary Examiner*—Gary L. Smith
*Assistant Examiner*—Flemming Saether
*Attorney, Agent, or Firm*—Patrick D. Kelly

[57] ABSTRACT

This invention relates to a protective restraint for patients such as sufferers of Alzhemier's disease or people emerging from anesthesia who, although not acutely violent or dangerous, must be restrained in a bed for their own safety. This device comprises a bottom portion called an anchor, which is placed under the mattress of a bed. A top portion called a topper is fastened to the anchor on both sides of the bed by means such as zippers which run along the sides of the anchor. For some uses, the topper can be translucent, such as nylon mesh, so that a caregiver can easily see the status of the patient and any bedclothes or catheters under the topper. For other uses and for additional warmth, an opaque sheet or blanket which extends beyond the edges of the anchor can be provided for maximal privacy and dignity. The topper is secured across the chest and shoulder region in a snug but not demeaning or severely uncomfortable manner. If necessary, additional restraint can be provided by means of an adjustable strap referred to as a snugger, which normally remains hidden from view. This device is quick and easy to secure or remove, and can be released partially from the foot end for cleaning the patient or other caregiving without a complete release or other disruption. It provides safe and convenient restraint with more comfort and dignity than any device previously available.

17 Claims, 3 Drawing Sheets

PROTECTIVE RESTRAINT FOR ALZHEIMER AND OTHER PATIENTS

FIELD OF THE INVENTION

This invention is in the field of protective restraining devices for patients suffering from Alzheimer's disease, senility, post-anesthesia disorientation, or other problems.

BACKGROUND OF THE INVENTION

A substantial and increasing number of individuals, especially among the elderly, must be either restrained or closely supervised because they create various risks, especially to themselves, if they are allowed to wander. This holds true even though such patients usually are not violent. For example, people suffering from severe Alzheimer's disease, senility, or dementia often lose the ability to reason or remember. Such people may wander off and become lost or get into threatening situations, especially late at night, when the people who normally supervise them are asleep and when institutions are not staffed to provide one-on-one care.

Due partly to the current shortcomings in the restraining options available to keep such people from hurting themselves, such patients often must be institutionalized, if the family can afford it or has adequate insurance (as used herein, institutions includes government-run facilities as well as privately operated nursing homes). If institutionalization is infeasible or undesired for financial, familial, or other reasons, caring for such patients (who often require constant attention) imposes a tremendous physical and emotional strain on the family or other caregivers, which often lasts for years with no hope of improvement.

Various devices and methods have been developed for restraining mentally impaired patients who, although not violent or acutely dangerous, need to be restrained primarily for their own safety. However, none of the devices currently available are fully satissfactory, and some suffer from severe shortcomings. Vest restraints and various types of straps or belts (such as "Posey" belts) are often wrapped around the arms, legs, or torsos of such patients, but they are highly unsatisfactory for several reasons They are often uncomfortable and can severely agitate the patients they are designed to restrain, causing them to struggle as hard as possible to escape.

In addition, the restraints previously used can inflict a severe loss of dignity on patients who want, need, and deserve respect and kindness. If a patient in an institution or nursing home shares a room with another patient who has a visitor, or if visitors come through on a tour, any visitors who see the straps that hold and tie down a restrained patient often shrink back out of fear and anxiety, wondering whether the restrained person might be violent or criminally insane. It can lead to intense discomfort, causing some visitors to refrain from visiting again and depriving patients of the companionship and pleasant distractions of having company.

In addition, there is a need for an improved restraint for surgical patients emerging from anesthesia. Such patients often awake in a disoriented and bewildered condition and, without having any desire to cause any difficulty, they occasionally try to get up and can tear out stitches. Such people need a gentle restraint that will keep them from trying to get out of bed.

The object of the subject invention is to provide an improved device for protectively restraining patients who suffer from various types of mental impairment. The inventors are a Nursing Home Administrator and a Licensed Social Worker who have extensive experience with patients who need this type of protective restraint. Based on that experience, they have developed and refined a restraining device which provides greater comfort and dignity than any other restraint previously available. This device is relatively quick and simple to secure in place, and to release when appropriate. It is safe, reliable, more comfortable, and less intrusive than belts, straps, or other devices of the prior art. In addition, it provides few or no external signs of being a restraining device, which provides maximal dignity and privacy for the patient without sacrificing safety and security.

SUMMARY OF THE INVENTION

The device of this invention relates to a protective restraint for patients such as sufferers of Alzheimer's disease who, although not acutely violent or dangerous, must be restrained in a bed, primarily for their own safety. This device comprises a bottom portion, herein called an anchor, which is placed under the mattress of a bed such as a standard single bed. A top portion, herein called a topper, is fastened to the anchor on both sides of the bed by suitable means, such as zippers which run along the sides of the anchor. For certain uses, the topper can be a translucent material such as a nylon mesh, so that a caregiver can easily see the status of the patient and any bedclothes or catheters under the topper. For other uses, an opaque sheet of material which extends beyond the edges of the anchor can be provided for maximal privacy and dignity. The topper is secured across the chest and shoulder region in a snug but not demeaning or severely uncomfortable manner. If necessary, additional restraint can be provided by means of an adjustable strap referred to herein as a snugger, which remains hidden from view. This device is quick and easy to secure and to remove, and it provides a safe and convenient means of restraint with greater comfort, dignity, and compassion than any restraining device previously available.

DESCRIPTION OF THE PREFERRED EMBODIMENTS

Figure 1:
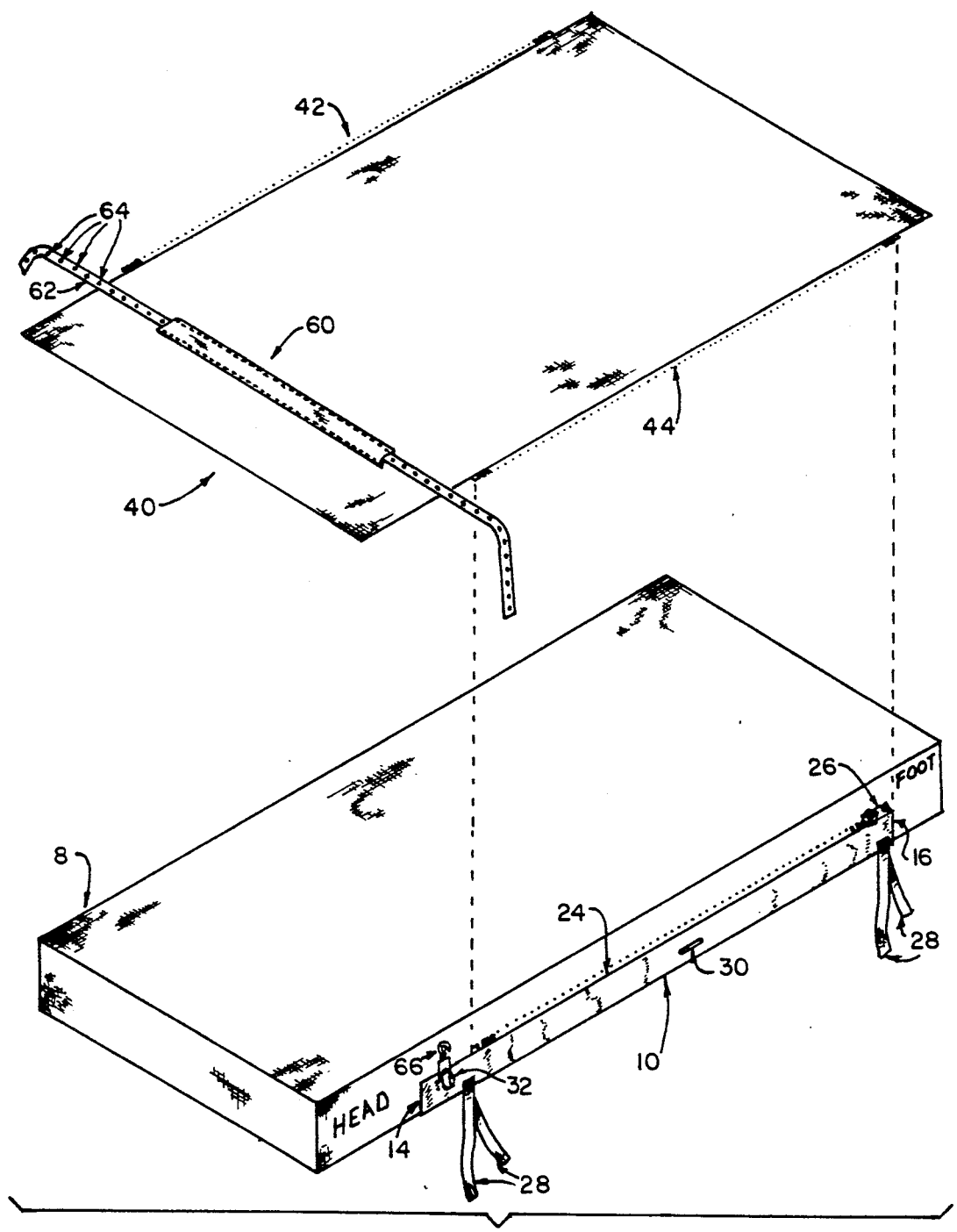
FIG. 1 is a side view which shows the anchor portion of the restraining device of this invention fitted beneath a mattress on a bed, with the topper portion aligned over the mattress and anchor.

One preferred embodiment of the subject invention comprises an anchor portion 10 coupled to a top portion 40 by means of zippers, as shown in FIG. 1. To assemble the system, the anchor 10 is laid flat and secured beneath the mattress 8 of a bed, such as a standard single bed. After the patient lies down on the mattress, the top portion 40 (referred to hereafter as the topper) is secured to the anchor 10. The top portion normally covers the shoulders, torso, and legs of the patient, while the patient's neck and head remain outside the cover.

Figure 2:
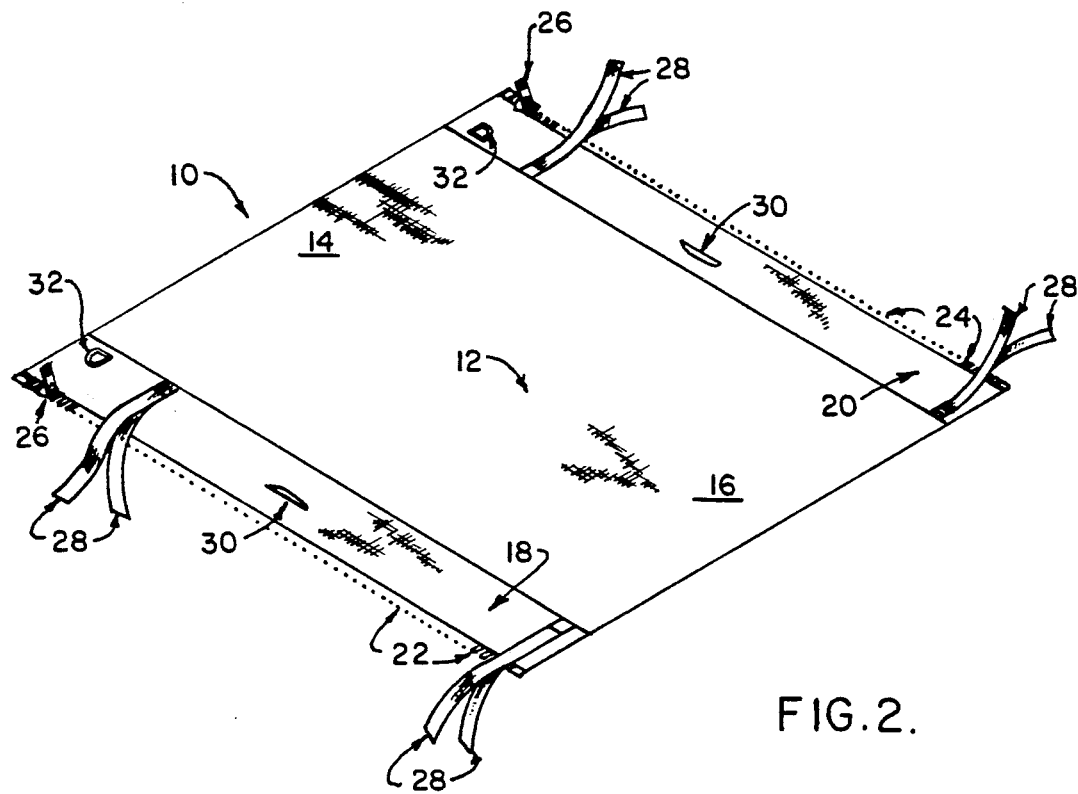
FIG. 2 provides a perspective view of the anchor portion of the subject invention, lying flat, as seen from the bottom.

As shown in FIG. 2, anchor portion 10 (hereafter referred to simply as the anchor) can comprise a central sheet 12, which has a head end 14 and a foot end 16 (all directions are designated according to the orientation of a patient lying face up on the bed). Peripheral side edges run the length of the anchor from the head end to the foot end; as used herein, "peripheral" and "side" refer to the edges that run alongside a patient's sides, as distinguished from the top and bottom sides of a piece of material.

In a preferred embodiment, portions of central sheet 12 become side portions 18 and 20, which are pulled up to a vertical orientation along the side of the mattress when the anchor 10 is secured to the topper 40. This makes the zippers or other attachment devices easily accessible to caregivers. For patients who are dextrous and act determined to exit this restraining device, steps may be taken as described below to ensure that the patient cannot release the attachment device, without severely hampering the ability of caregivers to open it, and without requiring the attachment device to be tucked beneath the mattress.

Side attachment means such as zipper portions 22 and 24 are attached along the edges of side portions 18 and 20. Each side attachment means will include a bottom segment (such as a row of zipper teeth, buttonholes, etc.) attached to the anchor, and a complementary top segment attached to the topper. When in use, zipper portions 22 and 24, which are affixed to anchor 10, will interact with zipper portions 42 and 44 which are affixed to topper 40. Preferably, a zipper is provided on each side, although that is not always necessary, as described below.

Preferably, the zippers should have nylon teeth to reduce the potential for scratching, and the teeth should be symmetric in such a manner that the topper can be secured to the anchor with either side facing up (i.e., either row of zipper teeth 42 or 44 will be able to mesh with zipper row 22, or with zipper row 24). Such zippers, which can be cut to any desired length from bolts of zipper material and fitted with end fittings at a manufacturing or vending facility, are sold by various companies, including tent and awning vendors. Preferably, the zippers should be detachable, so that the topper 40 can be detached from anchor 10. This will allow the topper to be removed and washed without having to move the anchor, which can remain under the mattress for months or years without becoming soiled.

It is not crucial whether the zippers are mounted with pull tabs 26 affixed to anchor 10, or to topper 40. Either way has certain advantages. If the pull tabs are mounted on the anchor, they will remain there each time the topper is removed and washed and dried, thereby reducing wear and tear on the pull tabs. However, if the pull tabs are mounted on the topper and the zipper teeth are symmetric in either direction, the topper can be zipped toward the feet at night, while the caregiver is asleep, and turned around and zipped toward the head during the day to allow the shoulder and chest region to be unzipped, which may be desirable to allow a patient to be propped up in an upright or semi-upright position for watching television or other activities, as described below.

In one preferred embodiment, the zippers are mounted so that the teeth begin their engagement at the head end of the anchor. The pull tabs 26 are pulled from the head end 14 toward the foot end 16 when the topper 40 is secured to the anchor 10. This will minimize the chance that the patient will be able to reach and manipulate either pull tab 26 to open either zipper. In an alternate embodiment, the pull tab can be secured to the end of the zipper (for example, a pull tab with a large slot in the middle of the tab can fit over a raised eyelet, and a cotter pin or other locking device can be pushed through the eyelet to secure the pull tab, as is done with some types of luggage. This can allow the pull tab to remain near the patient's head while the restraint is in use, which can be advantageous in some situations. For example, it may be desirable to unzip portion of the topper between the chest and the waist while the portion toward the feet remains secured, to allow the patient to be propped up in a sitting position. In such situations, the pull tabs can be secured near the middle of the bed by means of safety pins or other suitable devices.

If desired, the topper 40 and the central sheet of the anchor 10 can be made of a single piece of material, or of two pieces of material attached by a seam rather than a zipper. Although this would decrease the convenience and ease of use of the restraint, making it necessary to remove the anchor from beneath the mattress each time the topper is washed, it would eliminate the cost of one of the long zippers, as well as the associated cost of sewing the zipper or other side attachment means to the topper and anchor pieces.

Preferably, one or two bedframe straps 28 should be attached near each corner of anchor 10, so that anchor 10 can be securely attached to the bedframe. Such straps can comprise, for example, flat nylon straps with widths of 1 inch or greater, which can simply be tied to any portion of the bedframe. Although such attachment straps may not be necessary for some patients, they may become necessary later on as a debilitating process of mental deterioration grows worse. If not needed for any specific patient, the bedframe straps 28 can be tucked away and hidden under the mattress.

Central sheet 12 can be made of any suitable material with adequate strength. Materials such as canvas or rip-stop nylon are more durable than, for example, cotton or cotton-polyester sheets, and are therefore preferred. The exact dimensions of the topper and anchor portions can vary. Standard mattresses for single beds have dimensions within the ranges of 35 to 36 inches (width) by 78 to 80 inches (length) by 6 to 8 inches (depth). Since the anchor does not need to extend the full length of the mattress, it can have a length anywhere in the range of about 50 to 70 inches, with a preferred length in the range of about 60 to 65 inches. Its width should be sufficient to provide for several inches of material extending beyond the sides of the bed, to make it easier to reach and secure the zippers; for example, a width of about 44 inches (including the width added by the zipper teeth) provides about 4 inches of material extending beyond the sides of the mattress on each side, when the mattress is centered on the anchor. That peripheral material is pulled up against the vertical sides of the mattress when the unit is in use.

At least one side of the anchor 10 should be fitted with a slot 30 so that a urine-draining catheter tube can pass through the anchor material to a catheter bag or other receiving device. The would allow the bag to be detached and emptied without disturbing the patient. Such slots preferably should be placed on both sides of the anchor, for maximum convenience. Reinforcing for the slots can be provided with buttonhole stitching, iron-on adhesive, or any other reinforcing means.

A snugger loop 32 (referred to in the claims as a "strap attachment means") should be attached to each side of the anchor. Those two loops, which can be made of nylon straps, plastic or metal loops, etc., will be used to secure the adjustable snugger strap 62 to the anchor, as described below, using a clipping device 66 at each snugger loop.

Since the sole purpose of anchor 10 is to provide a secure attachment means for topper 40, variations may be made to anchor 10 without infringing on its function. For example, instead of using a sheet of material to provide central sheet 12, a plurality of flat straps (such as nylon straps, 1.5 to 2 inches wide) can be used, by securing each end of each strap to a peripheral strap attached to a zipper portion. This configuration may be preferable if the mattress rests on a metallic support rather than cloth-covered bedsprings, as occurs in many institutions. Similarly, although zippers are a preferred side attachment means for at least one side, other side attachment means (such as a plurality of snaps, buttons, straps that interact with buckles, tie straps, or strips of Velcro) could be provided instead of zippers if desired, on either or both sides.

There are two different preferred embodiments of the topper. One embodiment, which offers maximal convenience for the caregiver, is likely to be preferable for use in many homes, where privacy is not a constant need. The other embodiment, which may be preferable for some institutional uses, offers maximum privacy and dignity for the patient. These will be referred to herein as the "sheer" topper 40 (shown in FIGS. 1 and 3) and the "blanket" topper 40A (shown in FIG. 4). If desired, both types of toppers can be purchased and used with a single anchor.

Figure 3:
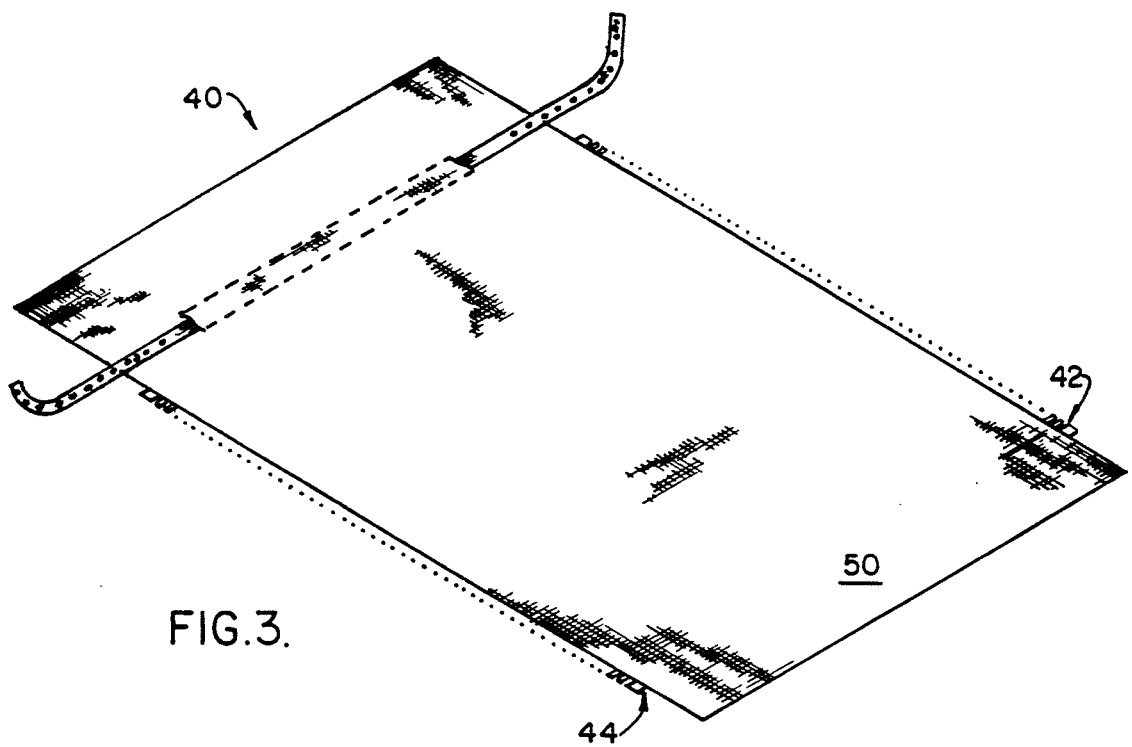
FIG. 3 provides a perspective view of a relatively transparent topper portion of the invention, as seen from the bottom, which provides a caregiver with simple visual monitoring of the patient.

In the sheer embodiment, as shown in FIG. 3, the topper 40 extends peripherally only to the zippers, without providing additional material which will drape down over the sides of the bed. Preferably, the material used in sheer toppers should be relatively transparent (such as a nylon mesh or sheer screen), so that the caregiver can monitor at a glance the condition of the patient and any bedsheets, catheters, etc.

Figure 4:
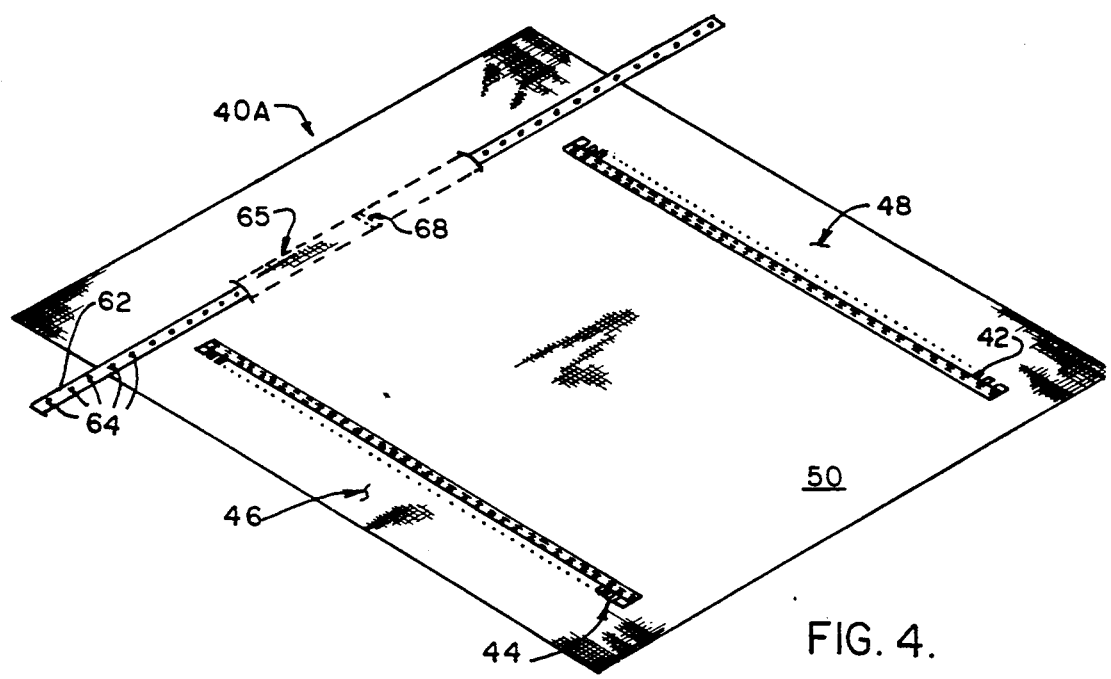
FIG. 4 provides a perspective view of a relatively opaque topper portion with side portions that drape over the edges of the bed and anchor, to provide maximal privacy for the patient.

In the blanket topper 40A, as shown in FIG. 4, side flaps 46 and 48 extend peripherally beyond the zippers, to provide extra material that drapes over the sides of the bed. Preferably, the material in this embodiment should be relatively opaque, such as bedsheet or blanket material. In institutions where regular bedchecks are required, this will provide maximal privacy and dignity to the patient without creating a risk that the patient might go for many hours with, for example, fecal soiling or bedsheets that have been shoved down to the foot of the bed. In that embodiment, the zippers are still referred to as side attachment devices because they run along the sides of the patient.

If desired, different toppers can be used at different times, having different thicknesses and warmth and ventilation characteristics. For example, a topper made of thick blanket material can be used during the winter, while a topper made of loose mesh can be used for maximum coolness during the summer.

After a patient lies down on the mattress, he or she can be covered with a bedsheet if desired, which will be held in place by the topper. The topper 40 or 40A is then secured to the anchor 10, using the zippers or other attachment means provided along the sides of each piece of material. If desired, the bedsheet and/or any other bedclothes (such as a blanket) can be placed on top of the topper, and can be secured in place if desired by clips, safety pins, or other means so that the patient will not dislodge them and cause them to fall to the floor.

Figure 5:
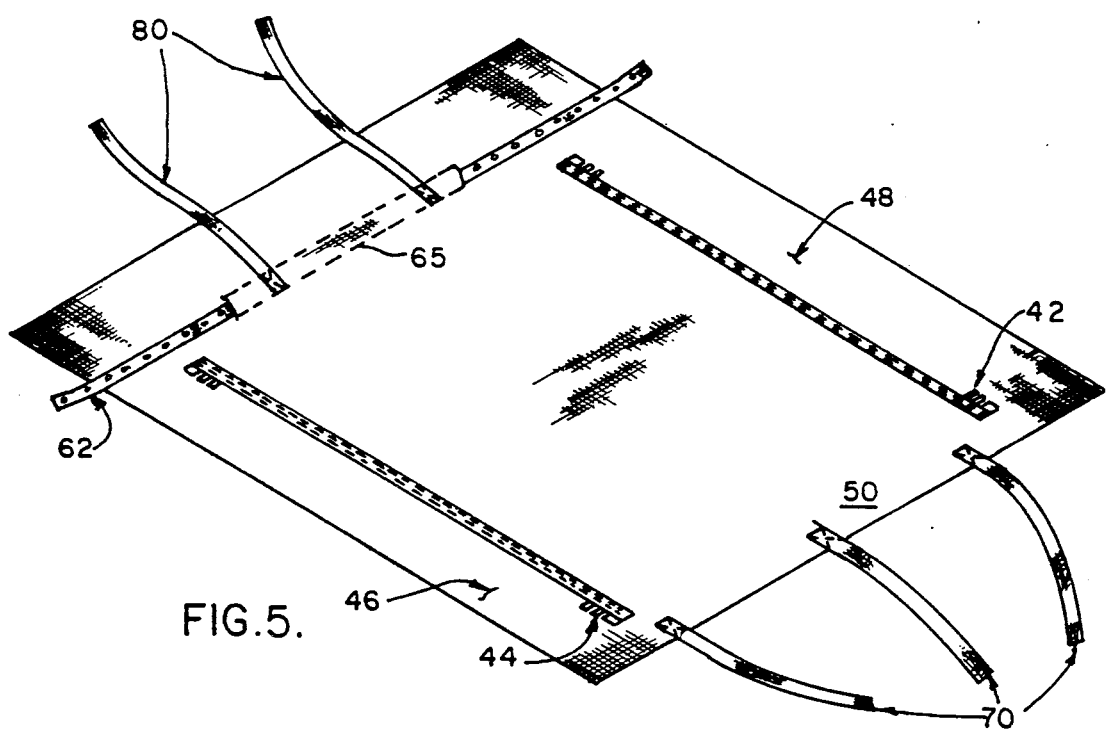
FIG. 5 provides a perspective view of a topper portion having straps at the foot end and head end.

Preferably, the topper should have a generous amount of material at the foot region, to create a foot flap 50. The foot flap 50 can be securely tucked beneath the foot of the mattress so that the patient cannot easily wriggle out of the restraining device through an opening at the foot. Toppers with lengths of about 90 inches have been shown to be satisfactory; since the head edge of the topper sheet does not reach all the way to the head of the mattress, this provides roughly 20 inches of material which extends beyond the foot of the mattress. Alternately, the foot region of the topper can be provided with one or more attachment devices such as straps 70, as shown in FIG. 5, which would allow the foot of the topper to be secured to a bedframe or any other secure object, such as a second strap attached to the anchor portion. Such straps can be equipped with sturdy snaps, buckles, or other attachment means which can be quickly disengaged to remove the topper quickly if a problem arises.

When the patient and the topper are in position, a portion of the topper referred to herein as the snugger 60 can be adjusted to pull the topper more snugly down on top of the patient. As shown in the figures, the snugger 60 lies at or near the chest and shoulder region of the patient and passes laterally (i.e., from side to side) across the chest or shoulders of the patient.

Preliminary tests with patients having varying ranges of physical dexterity and mental competence indicate that for most patients in need of protective restraint, a snugger strap is not necessary; a topper sheet alone is sufficient. However, providing a snugger strap (or means for conveniently attaching a snugger strap to the topper at a later date) in case a patient might need it, either during long-term care or during difficult episodes, is preferred. The snugger preferably comprises a snugger strap 62 which is provided with means so that the tension of the strap can be adjusted while in use. For example, strap 62 can be fitted with a plurality of attachment holes 64, which can be spaced evenly (such as every two inches or so) along the entire strap or a portion thereof.

In one preferred embodiment, snugger strap 62 passes through a fabric tunnel 65, created by sewing a strip of material onto the topper. Alternately, snugger strap 62 can pass through a plurality of loops comparable to belt loops, or it can simply lie outside the topper material if it is secured in the middle and at both ends. For ease of assembly, the snugger strap 62 can comprise a single strap which is affixed to the topper 40 using reinforced stitching 68 or other suitable attachment means (such as rivets) in or near the middle of the topper. Alternately, it can comprise two strap portions, both of which are sewed or otherwise affixed to the topper.

To adjust and secure the snugger, if needed, a clip or buckle device 66 is used at each end of snugger strap 62.

Any conventional type of clip or buckle can be used. Such clips can have a single clipping attachment at one end, if the clips are permanently affixed in the snugger loops 32 on the anchor 10. Alternately, double clips (each one having two clipping attachments, one at each end) can be used; this would allow the clips to be detached from the anchor (for example, when the anchor is washed).

One end of each clip 66 is secured, either temporarily or permanently, to a snugger loop 32 on the anchor; the other end of the clipping device 66 is passed through one of the holes 64 that pass through the snugger strap 62. The selected hole will provide the proper degree of tension on the snugger strap for a specific patient, depending on the size and needs of the patients. In some uses, the patient may need to be fully secured under the topper, with the snugger strap across the shoulders, restraining both arms under the topper. In other situations, one or both arms of certain patients can be allowed to remain outside the snugger, to give such patients a greater sense of freedom and control without allowing them to easily remove or leave the restraint.

After the snugger 60 has been secured, the head end of the topper 40 is folded over it, concealing the snugger. This causes the entire restraining device to take on the appearance of a normal blanket or other bed covering, so that visitors will not be taken aback or frightened by the appearance that the patient must be physically restrained.

For patients who need a more secure restraining device, it is possible to additional straps at various locations around the periphery of the topper. For example, patients who are agile and determined to exit the device can be restrained with greater security by incorporating two additional straps 80, one on each side of the patient's neck, attached to the snugger strap and passing from the snugger strap to the bedframe above the patient's head. Such straps can be permanently attached to the snugger if desired; alternately, they can be wrapped around the snugger strap and/or passed through reinforced slits in the topper material. The other end of each strap can be attached using snaps, buckles, or any other suitable means to any secure object, such as a bed frame or the anchor portion.

One advantage of this device is its ease of use and adjustment. For example, the anchor can be moved toward either the head or foot of the bed with fairly little difficulty, while the patient remains on the bed if necessary. In addition, the bottom half of the topper (or one corner thereof) can be unzipped and raised so the patient can be checked and cleaned if necessary, without removing the top half and without releasing the patient.

This restraint can be also be used with various types of specialized beds, such as hospital beds with head regions that can be tilted up to make it easier for a patient to talk, watch television, or do other activities where horizontal vision is desired. With some patients and bed types, there will be no need to modify any of the pieces described herein for such use; for other patients or bed types, various modifications can be made with little difficulty by any caregiver. For example, if a large cushion is used to raise a patient to a sitting or nearly sitting position to watch television, it may be necessary to unzip a portion of the topper between the chest and the waist, which can be done as described above. In such situations, the snugger strap can be used to provide a restraint around the chest.

Thus, there has been described a highly useful protective restraint, for use with patients who must be restrained for their own safety and security, which satisfies all of the objects and goals set forth herein. Although this device has been described with respect to certain embodiments, it will be apparent to those skilled in the art that various modifications may be made to those embodiments without departing materially from the spirit of this invention. Such equivalents are within the scope of this invention, which is limited only by the claims that follow.

I claim:

1. A restraining device for restraining an adult patient in a bed, comprising an anchor portion and a top portion, each of which has a head end, a foot end, two peripheral side edges spanning the distance from the head end to the foot end, and at least one side attachment device on each of said anchor and top portions which span at least part of the distance between the head end and the foot end, a chest strap, and strap attachment means for the chest strap, wherein:
   a. the anchor portion has a central portion with dimensions appropriate for it to be placed beneath a mattress that is suitably sized for an adult, wherein the peripheral side edges are accessible on each side of the mattress;
   b. the top portion has dimensions that allow it to be placed on top of the torso and legs of a patient lying on the mattress when the device is in use;
   c. the side attachment devices on the anchor portion and top portion interact with each other to securely connect the anchor portion to the top portion in a manner which, although disengageable by a person outside the restraining device, cannot be easily disengaged by the patient;
   d. the chest strap is affixed to the top portion near the head end and passes laterally across the chest of an adult patient when the restraining device is in use;
   e. the strap attachment means attaches the chest strap to the anchor portion in a manner that allows the tension in the chest strap to be adjusted when the restraining device is in use; and,
   f. the side attachment devices, the chest strap, and the strap attachment means are concealed by the top portion to generate an appearance that the patient is not being subjected to physical restraint.

2. The device of claim 1 wherein the side attachment means comprise at least one zipper, wherein the zipper comprises a top row and a bottom row of zipper teeth, said top and bottom rows being affixed to the top and anchor portions, respectively, of the restraining device.

3. The restraining device of claim 1 wherein the side attachment means comprise two zippers, one located on each side of the patient.

4. The restraining device of claim 1 wherein the side attachment means comprise a zipper on one peripheral side and a second type of attachment means located on the other peripheral side, wherein the second attachment means is selected from the group consisting of snaps, buckles, buttons, tie straps, and Velcro attachments.

5. A restraining device of claim 1 which is designed to allow a caregiver to visually monitor the status of the patient without removing or releasing any part of the top portion, wherein the top portion comprises a panel of material that is adequately translucent, meshed, or perforated to allow visual monitoring through the panel of material.

6. A restraining device of claim 1 wherein the top portion comprises a relatively opaque material to maximize the patient's privacy.

7. The restraining device of claim 6, wherein the top portion comprises regions of relatively opaque material which pass beyond the side attachment devices and which, when the restraining device is in use, hang below the sides of the mattress.

8. The restraining device of claim 1 comprising a foot-end attachment means coupled to the top portion of the restraining device, adjacent to the foot end of said top portion, wherein the foot-end attachment means is designed to couple the foot end of the top portion to a bed frame or other secure object.

9. The restraining device of claim 1 comprising at least two straps attached to the top portion of the restraining device near the head end, wherein said straps, when in use, restrain the shoulders of a patient on each side of the patient's neck and couple the top portion to a bed frame or other secure object.

10. The restraining device of claim 1 comprising at least two shoulder straps attached to the strap that is affixed to the top portion of the restraining device near the head end, wherein said shoulder straps, when in use, are affixed to a bed frame or other secure object and restrain the shoulders of a patient on each side of the patient's neck.

11. A restraining device for restraining a patient in a bed, comprising (a) a bottom portion designed to be placed beneath a mattress that is suitably sized for an adult, comprising a central portion that passes beneath the mattress and peripheral attachment means, (b) a top portion comprising a panel of material that covers a substantial portion of the patient when in use, and peripheral attachment means, wherein the peripheral attachment means on the top and bottom portions interact with each other to allow the top and bottom portions to be securely affixed to each other in a manner which, although disengageable by a person outside the restraining device, cannot be easily disengaged by the patient, (c) a strap affixed to the top portion near the head end, which passes laterally across the chest or shoulders of a patient when the restraining device is in use, and (d) strap attachment means which attaches the strap to the bottom portion in a manner that allows the tension in the strap to be adjusted while the restraining device is in use.

12. The device of claim 11 wherein the peripheral attachment means comprise at least one zipper, wherein the zipper comprises a top row and a bottom row of zipper teeth, said top and bottom rows being affixed to the top and bottom portions, respectively, of the restraining device.

13. The restraining device of claim 11 wherein the side attachment means comprise a zipper on one peripheral side and a second type of attachment means located on the other peripheral side, wherein the second attachment means is selected from the group consisting of snaps, buckles, buttons, and tie straps.

14. A restraining device of claim 11 which is designed to allow a caregiver to visually monitor the status of the patient without removing or releasing any part of the top portion, wherein the top portion comprises a panel of material that is adequately translucent, meshed, or perforated to allow visual monitoring through the panel of material.

15. A restraining device of claim 11 wherein the top portion comprises a relatively opaque material to maximize the patient's privacy.

16. The restraining device of claim 11 comprising a foot-end attachment means coupled to the top portion of the restraining device, adjacent to the foot end of said top portion, wherein the foot-end attachment means is designed to couple the foot end of the top portion to a bed frame or other secure object.

17. The restraining device of claim 11 comprising at least two straps attached to the top portion of the restraining device near the head end, wherein said straps, when in use, restrain the shoulders of a patient on each side of the patient's neck and couple the top portion to a bed frame or other secure object.

* * * * *